US005547460A

United States Patent [19]

Ishikawa

[11] Patent Number: 5,547,460

[45] Date of Patent: Aug. 20, 1996

[54] ROTARY PLATFORM FOR MEDICAL TREATMENT

[75] Inventor: Kiyoshi Ishikawa, Ako, Japan

[73] Assignee: Akiko Ishikawa, Hyogo, Japan

[21] Appl. No.: 333,723

[22] Filed: Nov. 3, 1994

[30] Foreign Application Priority Data

Jan. 19, 1994 [JP] Japan .................................... 6-019922

[51] Int. Cl.[6] ...................................................... A61M 1/00

[52] U.S. Cl. ................................ 601/23; 601/84; 482/51; 482/146

[58] Field of Search ................................. 482/30, 51, 77, 482/79, 146, 147, 142; 472/14, 25, 26; 434/258, 260, 261; D21/193; 601/23, 27, 32, 84, 90, 92, 112, 1; 273/449

[56] References Cited

U.S. PATENT DOCUMENTS 2,707,465 5/1955 Nemeth .................................. 482/146
3,403,905 10/1968 Hamilton ................................. 601/23
3,859,736 1/1975 Hill et al. ............................... 482/146
3,936,047 2/1976 Brandt et al. .......................... 482/146
4,429,869 2/1984 Eckstein ................................. 482/146

FOREIGN PATENT DOCUMENTS 88643 9/1983 European Pat. Off. ............... 482/147
985069 3/1965 United Kingdom ..................... 472/25

*Primary Examiner*—Richard J. Apley
*Assistant Examiner*—Jeanne M. Clark
*Attorney, Agent, or Firm*—Marshall, O'Toole, Gerstein, Murray & Borun

[57] ABSTRACT

An apparatus for treating bowlegs, which is simple in structure and easy in operation, gives no pains to the patients, while keeping the patient in a very stable and safe condition. The apparatus comprises a stationary platform 1, a tilted rotary plate 3 being located inside the platform 1 and having, on its top, a tilted surface 4 in the form of an inverted cone, a motor 2 for turning the tilted rotary plate 3 together with a patient standing upright on the tilted surface 4, and a control panel 7 for controlling the speed of rotation of the motor 2. The tilted rotary plate 3 is connected to the motor 2 in such a way that the plate 3 can be replaced with one of other tilted rotary plates having different angles of inclination.

5 Claims, 1 Drawing Sheet

ROTARY PLATFORM FOR MEDICAL TREATMENT

FIELD AND BACKGROUND OF THE INVENTION

The present invention relates to rotary platforms for medical treatment, and in particular, it relates to the configuration of a rotary platform mainly used for treating genu varum or so-called bowlegs.

The number of people who need medical treatment for a condition known as bowlegs, which is unique to the Japanese, has been growing more and more in recent years, and better treatment methods for the condition are needed. At present, however, no significantly effective treatment method has been established except for surgical operations. There are two or three conventional methods which have been practiced over the years. When the soles of the feet of a patient afflicted with bowlegs are examined from the front, both soles of the feet face upward and outward. To correct them to face upward and inward, one treatment method is to place liners in the shoes of the patient. Each liner is arranged to be thick on the outer side and thin on the inner side, forming an inclined surface. The angle of its inclination is set to suit the degree of bowing of the leg. During the progress of the treatment, the liners are replaced periodically with those of smaller degrees of inclination.

According to another treatment method, the patient is made to lie on her or his side in such a way that the curved portion of one leg is lifted from a horizontal plane. A pressure in the direction of gravity is applied to the lifted portion little by little without any excessive strain. The process is repeated for both legs to gradually decrease the degree of bowing and eventually restore the legs to the normal condition.

The treatment of bowlegs according to the above-mentioned methods has the following problems: With regard to the method wherein liners are placed in the shoes, it is necessary to successively replace the liners and/or the shoes structured specially for the purpose with new ones, according to the progress of the treatment. It, therefore, is costly. Moreover, some patients may have difficulties in walking or find it impossible to walk at all.

Next, with regard to the method wherein pressure is applied on the sides of the legs, the process of repeatedly applying the pressure itself is very difficult to make, and may cause pain to the patient. It is a method accompanied by many difficulties.

The present inventor has also invented an apparatus described in the Japanese Provisional Utility Model Publication No. HEI 4-4766. The apparatus includes a tread plate for the feet, which is flat and is arranged to be tilted forward in the downward direction from the horizontal position. The apparatus, therefore, has no effect of correcting genu varum or bowlegs. Moreover, it is difficult for feeble and/or aged patients to use the apparatus since the apparatus turns with the standing patient tilted forward. In particular, with the use of the tread plate, there is no space for providing a handrail for holding the body during the movement.

SUMMARY OF THE INVENTION

The present invention was made to overcome the problems of the above-described treatments. This is accomplished by providing a rotary platform which is simple in structure and easy in operation, gives no pains to the patients, and mainly treats bowlegs, while keeping the patient in a very stable and safe condition.

To solve the above-mentioned problems, the rotary platform according to the present invention comprises a stationary platform having an internal hollow, a tilted rotary plate, and a control panel. The tilted rotary plate is located inside the internal hollow, is shaped into an inverted cone having a tilted surface descending towards the center thereof, and is turned by a motor together with a patient standing on the plate with the soles of her or his feet placed on the tilted surface. The control panel controls the rotating speed of the motor. The tilted rotary plate is connected to the motor in such a way that the plate can be replaced with other plates having different angles of inclination.

It is preferred that the angle of inclination of the tilted surfaces of the tilted rotary plates of the rotary platform be set within the range of from 10 degrees to 45 degrees.

The top surface of each of the tilted rotary plates may be provided with a removable handrail.

To provide medical treatment to a patient using the rotary platform of the present invention, the shaft of the motor mounted in the middle of the rotary platform is inserted into a tilted rotary plate having an angle of inclination selected according to the degree of bowing of the legs of the patient. Then the patient, who has been made to wait on the platform, is guided onto the tilted rotary plate located at the center. The patient is made to place her or his feet on the tilted surface of the tilted rotary plate and stand upright. With the patient kept in this condition, the therapist controls the control panel to gently start the rotation of the tilted rotary plate, then gradually raises the speed to the desired level. When the desired speed is reached, the rotation of the plate is maintained for a desired period to treat the bowlegs.

If the angles of inclination of the above-mentioned tilted rotary plates are kept within the range of from 10 degrees to 45 degrees and a plurality of tilted rotary plates, the angles of which differ from each other within the range, are provided, a carefully planned treatment can be provided by sequentially exchanging tilted rotary plates of different angles of inclination according to the degree of the patient condition or according to the progress of healing.

If a removable handrail is provided on the top of the tilted rotary plate, the patient under treatment can hold the handrail to avoid the danger of toppling down on the tilted rotary plate. Moreover, even if the patient does not hold the handrail, the provision of the handrail gives the patient a sense of safety. Thus the treatment can be given to the patient who is calm in mind.

BRIEF DESCRIPTION OF THE DRAWINGS

The invention will be better understood from the following description and from the attached drawings, wherein.

DETAILED DESCRIPTION OF THE INVENTION

Figure 1:
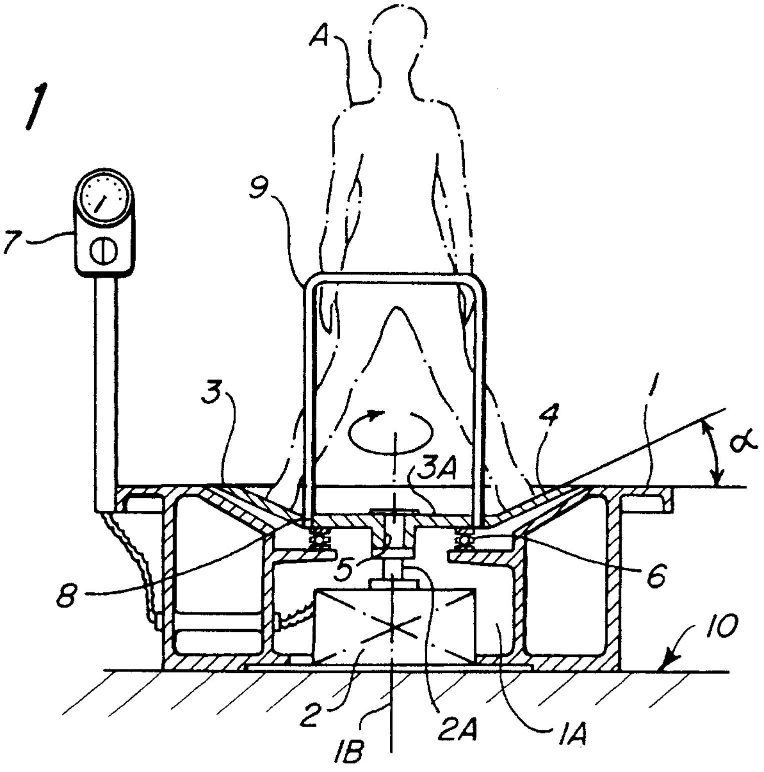
FIG. 1 is a sectional view illustrating the use of a rotary platform constructed according to an embodiment of the present invention.
Figure 2:
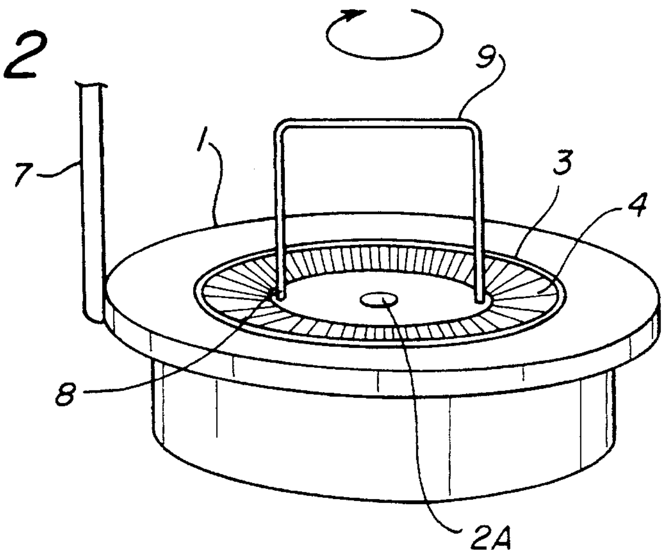
FIG. 2 is a perspective view of the rotary platform.

With reference to the drawings the reference numeral 1 denotes a stationary platform which has a horizontal upper surface when the machine is placed on a horizontal support 10. The platform 1 has a doughnut or annular shape with an internal circular hollow area 1A in which a motor 2 is mounted. The numeral 3 denotes a tilted or dished rotary plate, the top surface of which is formed into an inverted cone; it has a tilted or annular slanted surface 4 which tilts downwardly towards the center. The tilted rotary plate 3 has a horizontal center area 3A with a hole 5 at its centers into which the shaft 2A of the motor 2 is inserted. The platform 1 and the surface 4 are coaxial on a vertical center axis 1B, and the motor shaft 2A rotates on the axis 1B. When a patient A is treated, the patient A is made to place the feet on the tilted surface 4 and to stand upright, and then the patient A in this position is rotated together with the tilted rotary plate 3 around the central axis 1B by the motor 2. A bearing 6 is provided between the lower surface of the tilted rotary plate 3 and the stationary platform 1 to prevent any excessive load from being applied to the shaft 2A of the motor 2 by the weight of the patient A. The numeral 7 denotes a control panel which controls the speed of rotation of the motor 2.

Figure 3:
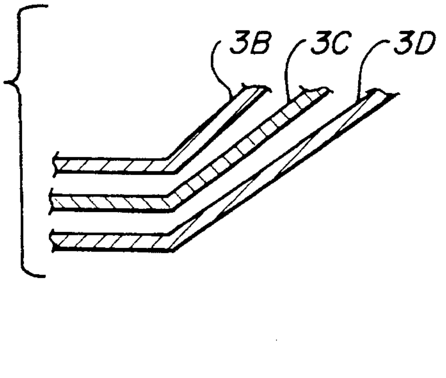
FIG. 3 is a sectional view of rotary plates of the rotary platform.

The tilted rotary plate 3 is connected to the shaft 2A of the motor 2 with a key in such a way that the plate 3 can be replaced by any one of other tilted rotary plates (see Fig. 3) having different angles ∝ of inclination. Treatment is given by frequently replacing the plate 3, having a relatively small pitch, with another tilted rotary plate having an optimal angle ∝ of inclination appropriate at the time according to the degree of the condition of the patient, or according to the progress of healing. The required angle of inclination ∝ is in the range of from 10 degrees to 45 degrees. A set of tilted rotary plates may comprise, for example, those having angles of inclination which are at intervals of five degrees within the range of from 10 degrees to 45 degrees, such as 10°, 15°, 20°, 25°, 30°, . . . . FIG. 3 illustrates a set of such additional rotary plates 3B, 3C and 3D having different angles of inclination. Generally speaking, the above-mentioned angle of inclination ∝ has a high frequency of use in the range of from 10° to 30°.

The top surface of the center area 3A of the tilted rotary plate 3 is provided with holes 8 for the insertion of a handrail 9. A removable handrail 9 may be erected, when necessary, on the top surface of the tilted rotary plate 3.

In giving a treatment to a patient suffering from bowlegs using the rotary platform of the above-mentioned construction, the procedure is as follows:

i) A tilted rotary plate 3 having an angle of inclination which is optimal at the time is selected and connected to the shaft 2A of the motor 2.

ii) If necessary, the handrail 9 is erected by inserting it into the holes 8.

iii) The patient A is guided onto the stationary platform 1. The patient A is made to gently place her or his feet on the tilted surface 4 of the tilted rotary plate 3 which is stationary at the time. The patient A may use the handrail 9 in this process. Then the patient A is made to stand upright.

iv) The therapist adjusts the control panel 7 to gently start the rotation of the tilted rotary panel 3, and gradually raise the speed of rotation to the desired level. When the desired speed is reached, the rotation will be maintained at that speed for a desired period. The speed of rotation of the tilted rotary plate 3 is about 5 R.P.M. for the beginners. As the patient progresses in the time of treatment, the speed of rotation is increased gradually. The maximum speed of rotation is around 50 R.P.M.

v) When the treatment is completed, the above-mentioned procedure is reversed. The rotation of the tilted rotary plate 3 is terminated and then the patient A is gently guided to the stationary platform 1.

vi) At the treatment of next time, the tilted rotary plate is replaced by one having a different angle of inclination, if necessary, and the above-mentioned procedure will be repeated. The angle gradually becomes steeper as the treatments progress.

With regard to the state of engagement of the ends of the handrail 9 and the holes 8 when the handrail 9 is erected on the tilted rotary plate 3, the use requirements of the handrail 9 vary, every time, according to the individual conditions of the patient or the speed of rotation for treatment. It, therefore, is necessary to make an arrangement for frequent engagement and disengagement; the state of engagement must assure easy engagement and disengagement and safe service of the handrail 9.

A rotary platform in accordance with the present invention having the construction described above, has the following effects and advantages.

Due to being restrained by the angle of the tilted surface of the tilted rotary plate, the corrective forces applied to the legs of the patient are loaded, under very natural conditions, as component forces working in the directions opposite to the bending directions of the bowing of the legs. Hence pains are not inflicted on the patient, and the patient can receive a comfortable treatment. With regard to the loads given to the patient, because the patient is positioned virtually on the exact center of rotation, the treatment to both the right and left legs is even and not biased to either side, producing balanced treatment effects.

Carefully planned treatment can be administered to the patient by replacing tilted rotary plates of different angles from one to another according to the degree of condition of the patient or according to the progress of healing. Thus a comfortable and rational treatment can be given.

For patients who feel anxiety about standing upright alone on a rotating tilted rotary plate, or who can not sustain that posture for a certain period of time, the provision of the handrail improves the treatment efficiency by allowing the patient to hold it. Moreover, even if the patient does not actually hold it, the handrail gives the patient a sense of safety that she or he can hold it at anytime. Thus the treatment can be given to the patient in a calm state of mind.

The described rotary platform has, in addition to the treatment of bowlegs, the following therapeutic effects. The therapeutic effects on human bodies of a rotary treatment with the rotary platform of the present invention or the rotary platform described in the Provisional Utility Model Publication No. HEI 4-4766 will be described in the following. In the treatment, a patient is made to stand on the tilted rotary plate 3 or the tread plate and the patient is subjected to rotary stimulation.

What is claimed is:

1. A rotary platform comprising a stationary platform having an internal hollow area, a tilted rotary plate located inside said internal hollow area, said plate being in the shape of a truncated inverted cone and having a tilted surface sloping at an angle towards the center thereof, a motor connected to said plate for rotating said plate together with a patient standing on said plate with the soles of her or his feet placed on said tilted surface, means connected to said plate for holding said plate for rotation on a substantially vertical axis, said plate being removably connected to said motor whereby said plate is adapted to be used with another selected tilted rotary plate having a different angle of inclination, and a handrail attached to said plate for steadying a patient.

2. A rotary platform as set forth in claim 1, wherein the angles of inclination of said tilted surfaces of said tilted rotary plates are set within the range of from 10 degrees to 45 degrees from horizontal.

3. A rotary platform as set forth in claim 1 or claim 2, wherein said handrail is removably mounted on said plate.

4. An assembly comprising a stationary platform having an internal hollow area, a set of tilted rotary plates, each of said plates including a surface portion having the shape of a truncated inverted cone with a tilted surface sloping at an angle towards the center thereof, said angles of slope of said plates of said set being different and within the range of from substantially 10° to substantially 45° from horizontal, a selected one of said plates being rotatably mounted in said internal hollow means, a motor connected to rotate said selected one of said plates together with a patient standing on said tilted surface on a substantially vertical axis, said selected one of said plates being removable and replaceable by another plate of said set.

5. An assembly as set forth in claim 4, and further comprising a removable handrail provided on said selected one of said plates for steadying the patient.

* * * * *